(12) United States Patent
Riley

(10) Patent No.: US 8,486,928 B2
(45) Date of Patent: Jul. 16, 2013

(54) SUPER-OXIDE DISMUTASE MIMETICS

(75) Inventor: Dennis P. Riley, St. Louis, MO (US)

(73) Assignee: Galera Therapeutics, St. Louis, MO (US)

( * ) Notice: Subject to any disclaimer, the term of this patent is extended or adjusted under 35 U.S.C. 154(b) by 427 days.

(21) Appl. No.: 12/740,399

(22) PCT Filed: Nov. 14, 2008

(86) PCT No.: PCT/US2008/083666
§ 371 (c)(1),
(2), (4) Date: Apr. 29, 2010

(87) PCT Pub. No.: WO2009/065059
PCT Pub. Date: May 22, 2009

(65) Prior Publication Data
US 2010/0256178 A1 Oct. 7, 2010

Related U.S. Application Data

(60) Provisional application No. 60/988,003, filed on Nov. 14, 2007.

(51) Int. Cl.
*A61K 31/33* (2006.01)
*C07D 487/00* (2006.01)

(52) U.S. Cl.
USPC ............................ 514/183; 540/471; 540/472

(58) Field of Classification Search
None
See application file for complete search history.

(56) References Cited

U.S. PATENT DOCUMENTS

| | | | |
|---|---|---|---|
| 5,610,293 | A | 3/1997 | Riley et al. |
| 5,624,677 | A | 4/1997 | El-Rashidy et al. |
| 5,637,578 | A | 6/1997 | Riley et al. |
| 5,874,421 | A | 2/1999 | Riley et al. |
| 6,180,620 | B1 | 1/2001 | Salvemini |

OTHER PUBLICATIONS

Yasui. Free Radical Research, 2005, 39(7), 755-762.*
Sessler. Chemistry: A European Journal, 1995, 1(1), 56-67.*
Bannister, J. V. et al, "Aspects of the Structure, Function, and Applications of Superoxide Dismutase," Crit. Rev. Biochem., 22, pp. 111-180 (1987).
Gryglewski, R. J. et al, "Superoxide Anion is Involved in the Breakdown of Endothelium-derived Vascular Relaxing Factor," Nature, vol. 320, pp. 454-456 (1986).
McCord, J., "Superoxide Dismutase: Rationale for Use in Reperfusion Injury and Inflammation," Free Radicals Biol. Med. 2, 307 (1986).
Palmer, R. M. J. et al., "Nitric Oxide Release Accounts for the Biological Activity of Endothelium Derived Relaxing Factor," Nature, vol. 327, pp. 524-526 (1987).
Petkau, A., "Scientific Basis for the Clinical Use of Superoxide Dismutase," Cancer Treat. Rev. 13, 17-44 (1986).
Riley, D. P., et al., "Rational Design of Synthetic Enzymes and Their Potential Utility As Human Pharmaceuticals: Development of Manganese(II)-Based Superoxide Dismutase Mimics," Adv. Supramol. Chem., vol. 6, pp. 217-244 (2000).
Riley, D. P., "Synthesis, Characterization, and Stability of Manganese (II) C-Substituted 1, 4, 7, 10, 13-Pentaazacyclopentadecane Complexes Exhibiting Superoxide Dismutase Activity," J. Inorg. Chem. vol. 35, pp. 5213-5231 (1996).
Simic, M. G. et al., "Introduction to Peroxidation and Antioxidation Mechanisms" in Oxygen Radicals in Biology and Medicine, Basic Life Sciences, vol. 49, Plenum Press, New York and London, pp. 1-10, (1988).
Weiss, J. "Catalytic Efficacies of Agents That Dismutate Superoxide," Cell. Biochem., vol. 47, 1991 Suppl. 15C (S15C), p. 216, Abstract C110 (1991).
Aston, K., et al., "Computer-Aided Design (CAD) of Mn(II) Complexes: Superoxide Dismutase Mimetics with Catalytici Activity Exceeding the Native Enzyme," Inorganic Chemistry, vol. 40, No. 8, pp. 1779-1789 (2001).
Riley, D., et al., "Toward the Rational Design of Superoxide Dismutase Mimics: Mechanistic Studies for the Elucidation of Substituent Effects on the Catalytic Activity of Macrocyclic Manganese(II) Complexes," JACS, vol. 119, No. 28, pp. 6522-6528 (1997).
Salvemini, D. et al., "A Nonpeptidyl Mimic of Superoxide Dismutase with Therapeutic Activity in Rats," Science, vol. 286, pp. 304-306 (1999).
Salvemini, D. et al., "M40403: Superoxide Dismutase Mimetic," Drugs of the Future, vol. 25, No. 10, pp. 1027-1033 (2000).
Salvemini, D. et al., "SOD Mimetics are Coming of Age," Nature Reviews, vol. 1, pp. 367-374 (2002).
Czapski, G., et al., "The Uniqueness Both of Superoxide Toxicity and of the Protective Role of Superoxide Dismutase" in Oxygen Radicals in Biology and Medicine, Basic Life Sciences, vol. 49, Plenum Press, New York and London, pp. 43-46, (1988).

* cited by examiner

*Primary Examiner* — Nobel Jarrell
(74) *Attorney, Agent, or Firm* — Bryan Cave LLP

(57) ABSTRACT

The present invention relates to compounds which are effective as catalysts for dismutating superoxide and, more particularly, the manganese or iron complexes of substituted, unsaturated heterocyclic 16-membered macrocyclic complexes that catalytically dismutate superoxide. It also relates to methods of using these complexes to reduce the concentration or the effects of superoxide, pharmaceutical compositions comprising these compounds or their metal complexes, and methods of treating conditions associated with excessive superoxide activity.

23 Claims, 2 Drawing Sheets

SUPER-OXIDE DISMUTASE MIMETICS

CROSS REFERENCE TO RELATED APPLICATIONS

This application is a 371 National based on International Application No. PCT/US2008/083666, filed on Nov. 14, 2008, which claims priority to U.S. Provisional Application No. 60/988,003, filed Nov. 14, 2007. Each of these applications is incorporated by reference herein in its entirety.

TECHNICAL FIELD

The present invention relates to compounds which are effective as catalysts for dismutating superoxide and, more particularly, the manganese or iron complexes of substituted, unsaturated heterocyclic 16-membered macrocyclic complexes that catalytically dismutate superoxide. It also relates to methods of using these complexes to reduce the concentration or the effects of superoxide, and methods of treating conditions associated with excessive superoxide activity.

BACKGROUND ART

The enzyme superoxide dismutase catalyzes the conversion of superoxide into oxygen and hydrogen peroxide according to equation (1) (this process is often referred to herein and in the art as dismutation).

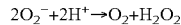

Reactive oxygen metabolites derived from superoxide have been demonstrated to contribute to the tissue pathology in a number of inflammatory diseases and disorders, such as reperfusion injury to the ischemic myocardium, inflammatory bowel disease, rheumatoid arthritis, osteoarthritis, atherosclerosis, hypertension, metastasis, psoriasis, organ transplant rejections, radiation-induced injury, asthma, influenza, stroke, burns and trauma. See, for example, Simic, M. G., et al., *Oxygen Radicals in Biology and Medicine*, BASIC LIFE SCIENCES, Vol. 49, Plenum Press, New York and London, 1988; Weiss, *J. Cell. Biochem.*, 1991 Suppl. 15C, 216 Abstract C110 (1991); Petkau, A., *Cancer Treat. Rev.* 13, 17 (1986); McCord, J. *Free Radicals Biol. Med.*, 2, 307 (1986); and Bannister, J. V., et al., *Crit. Rev. Biochem.*, 22, 111 (1987). In certain situations, cells are deficient in natural SOD activity; for example, this may occur as a result of heart attack, organ transplant, and even cancer: cancer cells are often deficient in SOD and can thus permit superoxide concentrations to rise and can cause injury to surrounding tissue.

It is also known that superoxide is involved in the breakdown of endothelium-derived vascular relaxing factor (EDRF), which has been identified as nitric oxide (NO), and that EDRF is protected from breakdown by superoxide dismutase. This suggests a central role for activated oxygen species derived from superoxide in the pathogenesis of hypertension, vasospasm, thrombosis and atherosclerosis. See, for example, Gryglewski, R. J. et al., "Superoxide Anion is Involved in the Breakdown of Endothelium-derived Vascular Relaxing Factor", *Nature*, Vol. 320, pp. 454-56 (1986) and Palmer, R. M. J. et al., "Nitric Oxide Release Accounts for the Biological Activity of Endothelium Derived Relaxing Factor", *Nature*, Vol. 327, pp. 523-526 (1987).

Clinical trials and animal studies with natural, recombinant and modified superoxide dismutase enzymes have been completed or are ongoing to demonstrate the therapeutic efficacy of reducing superoxide levels in the disease states noted above. However, numerous problems have arisen with the use of the enzymes as potential therapeutic agents, including lack of oral activity (a common problem with polypeptides), short half-lives in vivo, immunogenicity of nonhuman derived enzymes, and poor tissue distribution.

In an effort to overcome the problems associated with superoxide dismutase enzymes, several investigations have been made into the design of non-proteinaceous catalysts for the dismutation of superoxide, and their use in various superoxide-related ailments. One group of catalysts which has been shown to be nearly as effective catalysts as the native superoxide dismutase enzymes are the manganese and iron complexes of pentaazacyclopentadecane ligands, described in U.S. Pat. Nos. 5,610,293, 5,637,578, and 5,874,421. These ligands include a pentaazacyclopentadecane macrocycle with various substituents on the carbons of the macrocycle, or with cyclic or heterocyclic structures attached to the carbons of the macrocycle. Some of these complexes possess potent catalytic superoxide dismutating activity, and produce anti-inflammatory activity and prevent oxidative damage in vivo. In addition, these compounds, which are sometimes referred to as SOD mimetics, have been shown to possess analgesic activity and to reduce inflammation and edema in the rat-paw carrageenan hyperalgesia model, see, e.g., U.S. application Ser. No. 09/057,831. Exemplary compounds of this type include those shown in FIG. 1.

DISCLOSURE OF THE INVENTION

Applicants have found a new type of macrocyclic ligand that produces highly stable complexes with certain metals, including Mn and Fe, and provides improved activity as a SOD mimetic. The new macrocyclic ligands include a conjugated unsaturated 1,5-diaza group that deprotonates to provide a delocalized anion analogous to an acetylacetonate ligand (AcAc) ligand. This delocalized anionic group is an especially good bidentate ligand for certain metal cations: its affinity for the metal is increased by the ionic attraction between the anionic ligand and the metal. Applicants have found that incorporating this as part of a macrocyclic ring containing other nitrogen atoms provides SOD mimetics with especially potent activity. In addition, complexes of these ligands with a metal are less prone to dissociate at lower pH, possibly because the ligand has less tendency to become protonated to an extent that accelerates dissociation of a complexed metal cation. This five-atom subunit is incorporated into a 16-membered macrocyclic ring that is larger than the 15-membered rings previously described as SOD mimetics, and it introduces additional conformational control that may help stabilize the complex. Thus it provides SOD mimetic compounds with improved characteristics for certain applications.

In one aspect, the invention includes compounds of formula (1):

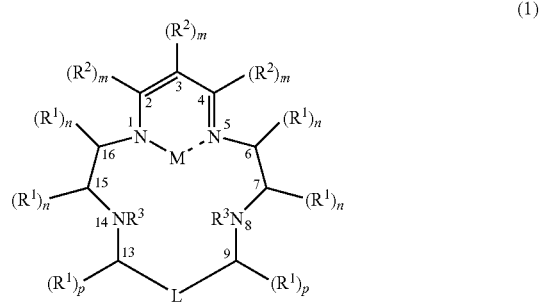

wherein:

each $R^1$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, =O, OR, $S(O)_tR$, $NR_2$, COOR, $CONR_2$, wherein t can be 0-2 and each R independently represents H, C1-C4 alkyl, and wherein two R groups on one N can cyclize to form a saturated azacyclic group;

each $R^2$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, OR, $S(O)_tR$, $NR_2$, COOR, $CONR_2$, wherein t can be 0-2 and each R independently represents H, C1-C4 alkyl, and wherein two R groups on one N can cyclize to form a saturated azacyclic group;

each $R^3$ is H or a protecting group;

wherein any two $R^1$ on a single carbon can cyclize to form a ring having 3-8 ring atoms, which ring can be substituted, and which can contain a heteroatom selected from N, O and S as a ring member;

and any two $R^1$ on adjacent carbon atoms, and any two $R^2$ groups on adjacent carbon atoms, can cyclize to form a ring having 3-8 ring atoms, which ring can be substituted and can be aromatic or non-aromatic, and can contain a heteroatom selected from N, O and S as a ring member;

and any two $R^1$ on carbon atoms separated by a single Nitrogen atom can cyclize to form a ring having 3-8 atoms, which ring can be substituted and can be aromatic or non-aromatic, and can contain, in addition to the N between the carbon atoms to which linked groups are attached, an additional heteroatom selected from N, O and S as a ring member;

and any two $R^2$ on carbon atoms separated by a single Nitrogen atom can cyclize to form a ring having 3-8 atoms, which ring can be substituted and can be aromatic or non-aromatic, and can contain, in addition to the N between the carbon atoms to which linked groups are attached, an additional heteroatom selected from N, O and S as a ring member;

each m is independently 0 or 1;

each n and p is independently 0-2;

L represents a three-atom linker that may be —C($R^1$)$_p$—$NR^3$—C($R^1$)$_p$— or an optionally substituted pyridine-2,6-diyl group; and M represents H or a metal cation;

or a pharmaceutically acceptable salt thereof.

In another aspect, the invention provides a compound of formula (2a):

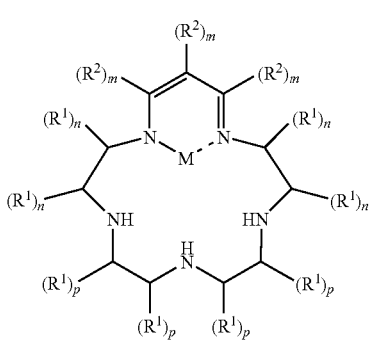

(2a)

wherein $R^1$, $R^2$, m, n, p and M are as defined for formula (1).

In another aspect, the invention provides a compound of formula (2b):

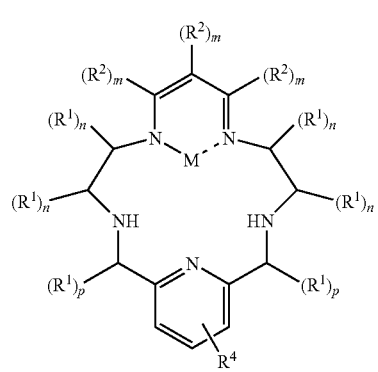

(2b)

wherein $R^1$, $R^2$, m, n, p and M are as defined for formula (1), and $R^4$ represents one or two optional substituents which may be present at any position(s) on the pyridine ring.

In another aspect, the invention provides compounds of formula (3):

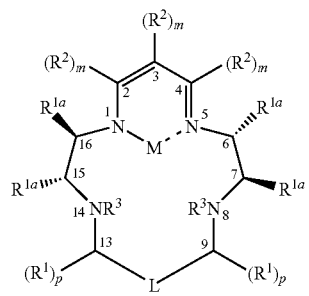

(3)

wherein $R^1$, $R^2$, $R^3$, L, m, p and M are as defined above for formula (1), and wherein $R^{1a}$ is an optionally substituted alkyl group, and wherein two $R^{1a}$ groups on adjacent carbons can link to form a ring.

The above compounds may be prepared as pharmaceutically acceptable salts or as prodrugs. Thus in another aspect, the invention includes the prodrugs of the compounds of formulas (1)-(3) and the pharmaceutically acceptable salts of these compounds and prodrugs As those of ordinary skill will appreciate, compounds of these general formulae can also be represented by other resonance structures or tautomeric structures wherein the double bonds of the macrocycle of formula (1) are not necessarily localized as shown. Those structures are equivalent for purposes of the invention: one tautomer is often depicted for convenience only and not to limit the invention. An equally appropriate way of representing a complex within the scope of the invention is this:

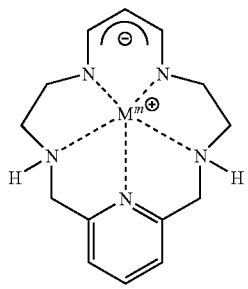

where $M^{m+}$ represents a metal cation that is bound symmetrically between the two nitrogens of the delocalized anionic binding portion shown at the top of the macrocycle, and is concurrently strongly coordinated to the other three nitrogen atoms in the macrocyclic ring, producing a powerful chelation effect.

These compounds and their pharmaceutically acceptable salts are useful as mimetics of the enzyme super oxide dismutase (SOD). Therefore, like SOD, they are useful to treat conditions where excessive superoxide is present or is likely to form. However, unlike SOD, the compounds of the invention are not prone to rapid degradation by proteolysis: they are therefore better for in vivo applications than SOD, because they tend to be longer lived and also can be administered orally. Because of their different structural and charge characteristics, they are often more stable and thus more potent in vivo and more effective upon oral administration than previously reported SOD mimetics.

In another aspect, the invention provides pharmaceutical compositions comprising a compound of formula (1), (2a), (2b), or (3) admixed with at least one pharmaceutically acceptable excipient. These compositions may be administered to a patient at risk of oxidative injury due to excessive superoxide formation, either alone or admixed with other active ingredients known to be beneficial for such patients, including drugs known to slow the formation or accelerate the decomposition of superoxide, and compounds that promote the decomposition of hydrogen peroxide, which is a less harmful but still oxidative material that is produced when superoxide is degraded by SOD or SOD mimetics. Likewise, the invention also provides methods of using the compounds described herein for the manufacture of a medicament.

In another aspect, the invention provides a method to reduce the concentration of destructive oxidative species, especially superoxide, in a locus where such destructive oxidative species are predicted to form. The method involves delivering a compound of formula (1), (2a), (2b), or (3) to the locus where such destructive oxidative species, typically superoxide, exist or are expected to form. This can include delivering a compound of formula (1), (2a), (2b), or (3) to a patient or applying it to a tissue, wherein the patient or tissue is at risk of injury caused by superoxide.

In other aspects, the invention provides methods to treat conditions associated with excessive superoxide formation. SOD mimetics have been shown to exhibit in vitro and in vivo activity in models for inflammation, myocardial ischemia-reperfusion injury, and vascular relaxation and restenosis. D. P. Riley, et al., *Adv. Supramol. Chem.*, vol. 6, 217-244 (2000). Specific conditions for which SOD mimetic compounds are reported to be useful include inflammatory diseases and disorders, such as reperfusion injury to the ischemic myocardium, inflammatory bowel disease, rheumatoid arthritis, osteoarthritis, atherosclerosis, hypertension, metastasis, psoriasis, organ transplant rejections, radiation-induced injury, asthma, influenza, stroke, burns and trauma, as well as for treatment of localized inflammation, edema, and pain. The compounds are also beneficial for treatment of certain aspects of neuronal apoptosis, cancer and acquired immunodeficiency syndrome (AIDS).

MODES OF CARRYING OUT THE INVENTION

Figure 1:
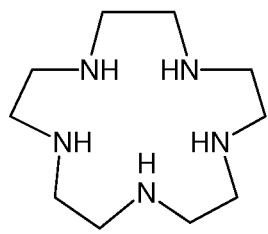
FIG. 1 depicts selected macrocycles reported to have activity as SOD mimetics.
Figure 1:
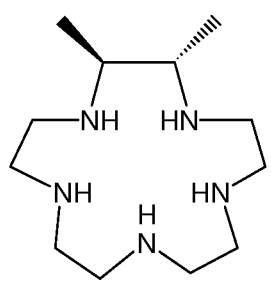
Figure 1:
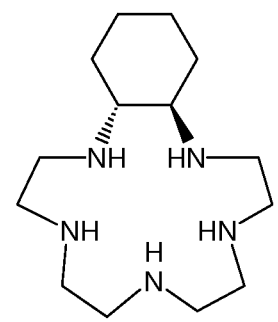
Figure 1:
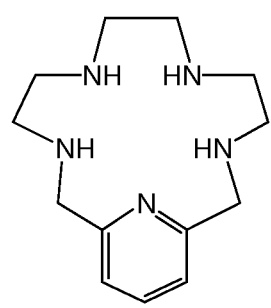
Figure 1:
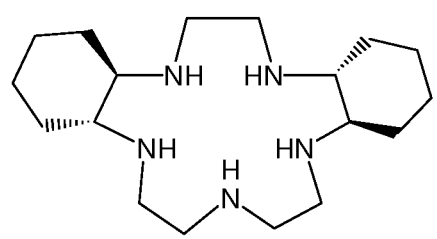

As used herein, "hydrocarbyl residue" refers to a residue which contains only carbon and hydrogen. The residue may be aliphatic or aromatic, straight-chain, cyclic, branched, saturated or unsaturated, or any combination of these. The hydrocarbyl residue, when so stated, however, may contain heteroatoms in addition to or instead of the carbon and hydrogen members of the hydrocarbyl group itself. Thus, when specifically noted as containing or optionally containing heteroatoms, the hydrocarbyl group may contain one or more heteroatoms as indicated within the "backbone" of the hydrocarbyl residue, and when optionally substituted, the hydrocarbyl residue may also have one or more carbonyl groups, amino groups, hydroxyl groups and other suitable substituents as further described herein in place of one or more hydrogens of the parent hydrocarbyl residue.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it may be described as 1-10C or as C1-C10 or as C1-10. When heteroatoms (typically N, O and S) are allowed to replace carbon atoms of an alkyl, alkenyl or alkynyl group, as in heteroalkyl groups, for example, the numbers describing the group, though still written as, e.g., C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with one or more groups selected from halo, =O, =N—CN, =N—OR', =NR', OR', NR'$_2$, SR', SO$_2$R', SO$_2$NR'$_2$, NR'SO$_2$R', NR'COOR', NR'COOR', NR'COR', CN, COOR', CONR'$_2$, OOCR', COR', and NO$_2$, wherein each R' is independently H, C1-C8 alkyl, C2-C8 heteroalkyl, C1-C8 acyl, C2-C8 heteroacyl, C6-C10 aryl or C5-C10 heteroaryl, and wherein two R or R' on the same or adjacent atoms can optionally cyclize to form a ring. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Preferably, each heteroalkyl, heteroalkenyl and heteroalkynyl group contains only one heteroatom or 1-2 heteroatoms. Such 'hetero' groups are, however, still linked to the base molecule via a carbon atom.

The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. Where such groups contain N, the nitrogen atom may be present as NH or it may be substituted if the heteroalkyl or similar group is described as optionally substituted. Where such groups contain S, the sulfur atom may optionally be oxidized to SO or SO$_2$ unless otherwise indicated. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to specifically describe a carbocyclic non-aromatic group that is connected via a ring carbon atom, and "cycloalkylalkyl" may be used to describe a carbocyclic non-aromatic group that is connected to the base molecule through an alkyl linker. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. The size of a cycloalkylalkyl or heterocyclylalkyl group describes the total number of carbon atoms or of carbon atoms plus heteroatoms that replace carbon atoms of an alkyl, alkenyl, alkynyl, cycloalkyl, or alkylenyl portion. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, e.g., —C(=O)R where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity, even though it may be fused to a nonaromatic ring. Typically, the ring systems contain 5-12 ring member atoms. Preferably the monocyclic heteroaryl groups contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, —C(O)R, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of group that comprises the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety.

An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane.

Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself be optionally substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not intended to be included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences and in accord with known principles of chemical stability; in particular, any of these groups may be substituted with fluorine atoms at any or all of the available valences on carbon atoms, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo", as used herein includes fluoro, chloro, bromo and iodo. Fluoro and chloro are often preferred.

"Amino" as used herein refers to NH$_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding type of group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, an 'azacyclic' group refers to a heterocyclic group containing at least one nitrogen as a ring atom, wherein the group is attached to the base molecule through a nitrogen atom of the azacyclic ring. Typically these azacyclic groups are 3-8 membered monocyclic rings or 8-12 membered bicyclic fused ring systems. An azacyclic group having more than four ring members can optionally include one additional heteroatom selected from N, O and S, and an azacyclic group having more than six ring members can optionally include one or two additional heteroatoms selected from N, O and S. Typically, an azacyclic group is non-aromatic, and such azacyclic groups can optionally be substituted with substituents that are suitable for alkyl groups. Typical examples of azacyclic groups include pyrrolidine, pyrrolidinone, piperidine, morpholine, thiomorpholine, and piperazine. In certain embodiments, an azacyclic group can be aromatic, provided that at least one ring nitrogen atom is in a five membered ring so the nitrogen can serve as the point of attachment to the base molecule. Examples of aromatic systems that can be azacyclic groups include pyrrole, imidazole, pyrazole, or indole.

The compounds of formulas (1)-(3) are 16-membered macrocyclic rings, and may be complexed to a metal M, or they may be metal-free, in which case M represents H. In preferred embodiments, M is H, Fe or Mn. For pharmaceutical compositions, typically M represents Mn or Fe, usually in a plus three oxidation state. In specific embodiments, M represents Mn(III). However, it is understood in the art that the superoxide dismutation process typically involves a metal center cycling between two different oxidation states, such as Fe(II)/Fe(III) or Mn(II)/Mn(III). Accordingly, the invention encompasses complexes wherein the metal cation is in any of these oxidation states.

Each $R^1$ in formulas (1)-(3) represents an optional substituent on a tetravalent carbon; valences of such carbons not occupied by a specified substituent such as $R^1$ are occupied by H as is understood in the art. In many embodiments, each $R^1$ present is an alkyl group such as methyl. In other embodiments two $R^1$ groups on adjacent carbons are linked to form a five or six membered saturated hydrocarbon ring (cyclopentane or cyclohexane) that is fused to the 16-membered macrocyclic ring, and such fused rings may be substituted. Such fused rings substantially influence the conformation of the macrocyclic ring, and may be positioned to enhance the SOD mimetic activity by favoring a conformation for the macrocycle that is conducive to complexation to a particular metal cation. In a preferred embodiment, at least one such ring is fused onto the macrocycle at positions 6 and 7 of the macrocycle, or at positions 15 and 16 of the macrocycle; in other embodiments, two such rings are fused onto the macrocycle, with one fused at positions 6 and 7, and the other fused at positions 15 and 16. These fused rings can be fused to the macrocycle with either a cis ring fusion or a trans ring fusion, as is understood in the art; and in preferred embodiments, a fused ring of this type is fused to the macrocycle with a trans ring fusion. Where two such fused rings are present, as when one such ring is fused onto the macrocycle at positions 6 and 7 of the macrocycle, or at positions 15 and 16 of the macrocycle, each such ring is preferably fused to the macrocycle in a trans fusion.

Each $R^2$ in formulas (1)-(3) independently represents an optional substituent on a trivalent carbon; valences of such carbons not occupied by a specified substituent are also occupied by H. Two $R^2$ groups on adjacent carbons can optionally be linked to form a fused ring, including a fused aromatic or heteroaromatic ring having five, or preferably six, ring members. In certain embodiments, $R^2$ at position 2 of the macrocycle represents methyl, or $R^2$ at position 4 of the macrocycle represents methyl, and in some embodiments $R^2$ at both positions 2 and 4 represent methyl.

Each n and each p in formulas (1)-(3) can independently be 0, 1 or 2; where n or p is 0, the corresponding carbon atom of the macrocyclic ring is unsubstituted, which means it has two hydrogens as is understood in the art. Where n or p is 1, the corresponding carbon atom of the macrocycle has one substituent and one hydrogen atom. Where n or p is 2, there are two $R^1$ groups on a single carbon of the macrocycle, and those two $R^1$ groups may cyclize to form a ring such as a cyclopropane having 3-8 ring atoms and optionally containing a heteroatom selected from N, O and S, and optionally substituted with the typical substituents that may be present on alkyl groups. In certain embodiments, each p is 0. In other embodiments p is 1 at two adjacent carbons of the macrocycle, and the corresponding $R^1$ groups may cyclize as further described below. In certain embodiments, n is 1 at one or more of positions 6, 7, 15 and 16 of the macrocycle. In some such embodiments, n is 1 at each of these positions, or at two adjacent positions. In such embodiments, two $R^1$ groups ma be on adjacent carbons of the macrocycle, and may cyclize as further described below. The compounds of formula (3) represent a particular embodiment where substituent groups represented as $R^{1a}$ groups are present on specified positions, and in formula (3) the relative stereochemistry of the $R^{1a}$ groups is also specified and corresponds to an orientation that provides particularly good SOD mimetic activity due apparently to preferentially maintaining an especially suitable conformation for the macrocycle to coordinate to M. Formula (3) illustrates a specific enantiomeric configuration, however, and the enantiomeric form of the SOD mimetics is not necessarily critical to their function. Accordingly, compounds that have the same relative configuration depicted in formula (3) but the opposite absolute stereochemistry, are expected to be similarly effective as SOD mimetics and are included in the invention. Thus formula (3) is understood to convey a preferred relative orientation for substituents $R^{1a}$ on the macrocycle but includes both enantiomeric forms of the macrocycle.

Similarly, where two $R^1$ or two $R^2$ groups are present on adjacent carbon atoms of the macrocycle, those two $R^1$ groups or two $R^2$ groups may cyclize to form a ring such as a cyclopropane, cyclopentane or cyclohexane having 3-8 ring atoms and optionally containing a heteroatom selected from N, O and S, and optionally substituted with the typical substituents that may be present on alkyl groups.

Each m in formulas (1)-(3) is independently 0 or 1; where m is 0, the corresponding carbon of the macrocycle has a hydrogen atom and no additional substituent. In certain embodiments, however, each m is zero, so no $R^2$ groups are present on the macrocycle.

Each $R^3$ in formulas (1)-(3) independently represents H or a protecting group that can readily be lost in vivo. As is understood, when M is a metal, it will be coordinated to each nitrogen having an $R^3$ group even though that relationship is not depicted expressly in the structures as drawn. In many embodiments, each $R^3$ represents H. However, if one or more $R^3$ represents a protecting group that can be cleaved under normal physiological conditions, the compound will still exhibit the desired physiological activity. Certain acyl groups, particularly trifluoroacetyl and other perfluoracyl groups, are examples of such protecting groups that dissociate from nitrogen in vivo and can provide biologically active SOD mimetics when administered. Accordingly, compounds wherein at least one $R^3$ group represents such a protecting group are included in the invention.

Compounds wherein one or more of the $R^3$ groups represents a protecting group that does not hydrolyze off under physiological conditions may not exhibit SOD mimetic activity in vivo. However, they are useful as precursors to the compounds wherein each $R^3$ is H, for example, and are thus still part of the invention. The use and particularly the removal of such protecting groups are well known in the art. Examples of suitable protecting groups for $R^3$ include, but are not limited to, formyl, acetyl, C1-C4 alkoxycarbonyl, trichloroacetyl, benzoyl, benzyloxycarbonyl, benzyl, and the like. Examples of such protecting groups and methods for the attachment and removal of such protecting groups are extensively documented in, for example, T. W. Greene's book entitled *Protective Groups in Organic Synthesis*, Wiley Intersciences, 2$^{nd}$ ed. (1991), which is incorporated herein by reference.

Typically, the SOD mimetic compounds of the invention are used as complexes wherein M represents a cationic metal species. The macrocyclic compounds, wherein M represents H, may be useful as prodrugs, because their affinity for chelating suitable metals in vivo is high: they can form active complexes with available metals such as $Fe^{3+}$ in the body. The non-complexed macrocycles are also useful as precursors to complexes wherein M represents a metal such as $Mn^{+3}$ or $Fe^{+3}$.

L in formulas (1) and (3) represents a three atom linker connecting the carbon atoms at positions 9 and 13 of the macrocycle. In some embodiments, L is $C(R_1)_p$—$NR^3$—$C(R^1)_p$ wherein $R^1$, p and $R^3$ are as described above. These correspond, for example, to compounds of formula (2a). In other embodiments, L represents a pyridyl ring that is attached to the macrocycle by the pyridyl carbons at positions 2 and 6, where the pyridyl ring is position 1 as it is conventionally considered to be. These correspond, for example, to compounds of general formula (2b). The pyridyl nitrogen then serves as one of the coordinating atoms for M if M represents a metal ion. Such pyridyl ring may be further substituted with substituent groups that are typically present on aromatic or heteroaromatic rings. In many embodiments, this pyridyl ring is not further substituted. In other embodiments it has one substituent that is at the 4-position on the pyridyl ring, and is preferably an optionally substituted C1-C4 alkyl or C5-C6 aryl group, or a heteroform of one of these groups. In certain embodiments, the pyridyl ring has one or two substituents. Preferred substituents if any are present, include phenyl, methyl, halo, especially chloro or fluoro, trifluoromethyl, trifluoromethoxy, and methoxy.

The compounds of the invention may and often do contain chiral centers, which may be included in the macrocycle or elsewhere. The invention expressly includes each enantiomer as well as each diastereomer of the compounds described and mixtures thereof, particularly racemic mixtures and highly enriched enantiomers having an enantiomeric excess (ee) of greater than 90% or greater than about 95%. Substituent groups may also include one or more chiral centers, and each enantiomer and diastereomer as well as mixtures thereof are all included within the scope of the invention. Similarly, where double bonds are present, the compounds can exist in some cases as cis or trans isomers; the invention includes each isomer.

Figure 2:
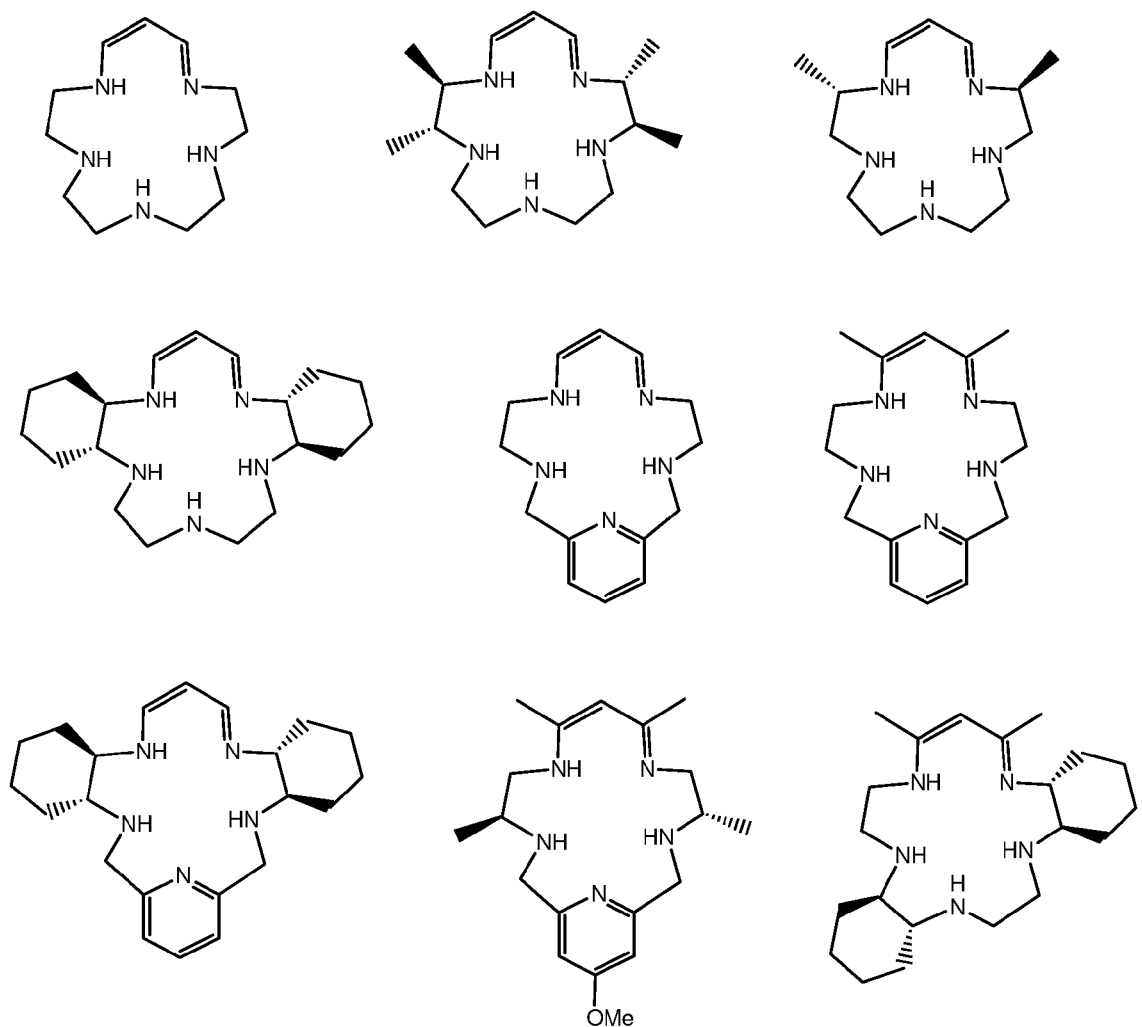
FIG. 2 depicts selected exemplary species within the current invention, showing only the neutral form of the molecule without a chelated metal.

Merely as examples of selected compounds of the invention, FIG. 2 illustrates a number of compounds of formula (1). These represent selected preferred species, and other species that include combinations of the features in the compounds specifically depicted are also preferred.

The compounds of the invention may be isolated as salts where an ionizable group such as a basic amine or a carboxylic acid is present. The invention includes the salts of these compounds, which are useful as intermediates and as precursors to the complexes of formulas (1)-(3). The complexes themselves may be considered salts in some instances, and may exist in various protonated forms depending on the nature of M and the pH of the environment. In particular, the pharmaceutically acceptable salts of the compounds of formulas (1)-(3) are included, because they are useful in the claimed methods and pharmaceutical compositions. Such salts are well known in the art, and include, for example, salts of acidic groups formed by reaction with organic or inorganic bases, and salts of basic groups formed by reaction with organic or inorganic acids, as long as the counterions introduced by the reaction are acceptable for pharmaceutical uses. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc.

Examples of organic bases that could be used include trimethylamine, triethylamine, pyridine, picoline, ethanolamine, diethanolamine, triethanolamine, dicyclohexylamine, N,N'-dibenzylethylenediamine, etc. Examples of inorganic acids that could be used include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

Compounds of the invention may be prepared using methods generally known in the art. In particular, the compounds of the invention are often prepared from a compound of formula (5) by reaction with a 1,3-dicarbonyl compound as illustrated in Scheme I. Suitable 1,3-dicarbonyl compounds of formula (6) are well known in the art.

Reactions of this general type are well known to proceed to produce certain ring structures; however, in preparing the macrocyclic compounds of the invention, conventional conditions are not very efficient due to polymerization and side reactions. Accordingly, the reaction depicted in Scheme I is typically performed in the presence of a multivalent metal cation that acts as a template to favor formation of the desired macrocycles and in the presence of an equivalent of base to accept a proton from the 1,3-dicarbonyl compound (6).

Scheme 1. General method for making macrocycles of formula (1).

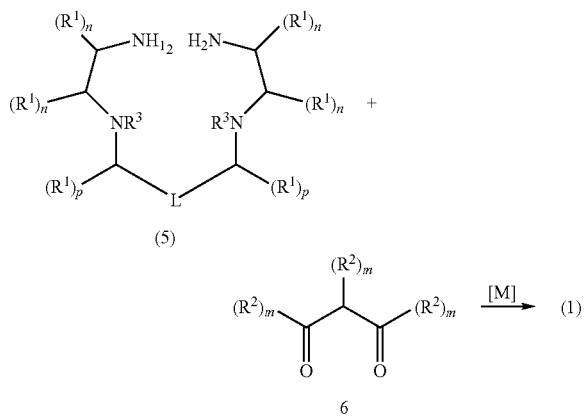

[M] represents a metal cation that is used to facilitate formation of the desired macrocycle.

Compounds similar to the intermediate of formula (5) and methods for their preparation are also known in the art; for example, applicable methods for their synthesis are described in D. P. Riley, et al., *J. Inorg. Chem.* vol. 35, 5213-31 (1996). Applicable methods are also described in U.S. Pat. No. 5,637,578 to Riley, et al., which is also incorporated herein by reference. Many of the synthesis methods in these references disclose synthesis of precursors having only three of the nitrogen atoms required for the macrocycles of the invention. Where these references describe preparation of such intermediates, the methods can be applied using conventional methods to introduce two additional nitrogen atoms in a protected form. For example, preparations of intermediates of formula (7) are reported, and these compounds can be converted into compounds of formula (5) as shown in Scheme 2. In formula (8) of Scheme 2, X represents a protecting functionality, and each $R^3$ is a protecting group suitable for reaction conditions that the molecule will be exposed to. The other groups are as defined for formula (1).

The reaction sequence in Scheme 2 requires the nitrogen atoms in formula (7) to be protected. The protecting groups used can be those used in the references, for example toluenesulfonate (Ts) can be used. However, a wide variety of alternative protecting groups such as benzyl, CBZ, tBOC, and various other acyl groups such as trichloroacetyl can also be used, and require only variations of conditions that are known to those of ordinary skill. Scheme 2 as shown indicates that a tosylate leaving group (OTs) can be employed; as those of skill in the art recognize, other leaving groups suitable for nucleophilic replacement can also be used.

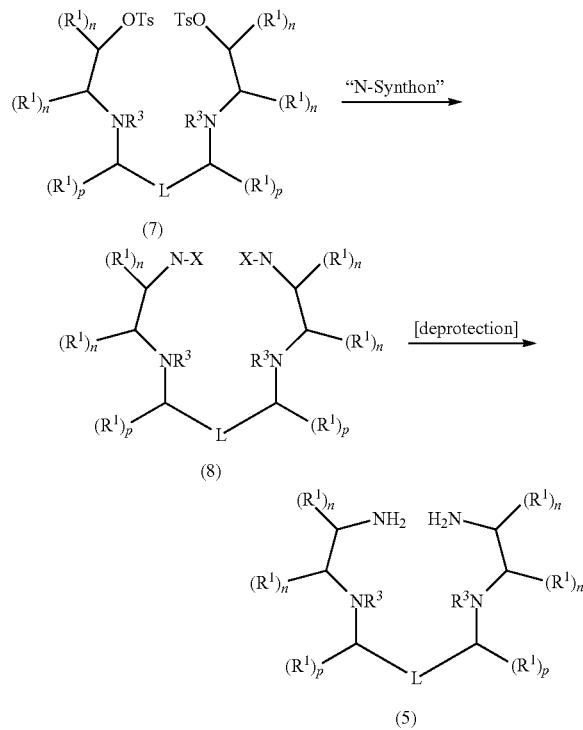

Scheme 2. General method for making intermediates for formula (5).

The "N-synthon" in Scheme 2 refers to a nucleophilic species that reacts with an alkylating agent such as compounds of formula (7) to place a nitrogen atom directly on the carbon where displacement occurs. A variety of suitable N-synthons are well known in the art; illustrative examples include azide ($N_3^-$) and phthalimide anion. These are efficient reagents that can be used to introduce the N—X groups depicted in formula (8), where X indicates that the nitrogen atom is in a protected form. If azide is used as the N-synthon, it can be reduced to form the amine of formula (5) using standard conditions such as, for example, catalytic hydrogenation. Likewise, if phthalimide anion (e.g., sodium phthalimide) is used, the phthalimide group can be removed using hydrazine or other conventional means. As those skilled in the art will appreciate, the selection of the N-synthon and the protecting group $R^3$ can be varied to accommodate a wide variety of substituents on the macrocycle precursors and to permit removal of X and/or $R^3$ at an appropriate time.

It is typically desirable to remove each $R^3$ and X in order to cyclize a compound of formula (8) or (5) using a metal cation as the cyclization template. In some embodiments, one or more $R^3$ groups may not be H when the cyclization is effected. The cyclization is best accomplished in the presence of a metal cation that provides a template to hold the acyclic polyaza compound of formula (5) in a suitable conformation to facilitate macrocycle formation. Suitable metal cations for this include, but are not limited to, Fe(II), Fe(III), Mn(II), Mn(III), and other transition metal cations having a plus two or plus three oxidation state.

The compounds of the invention can be used to prepare pharmaceutical compositions containing at least one compound of any of formulas (1)-(3). Such compositions can be optimized for various conditions and routes of administration using guidance that is widely relied on for such purposes including Remington's *Pharmaceutical Sciences*, latest edition, Mack Publishing Co., Easton, Pa., which is incorporated herein by reference. The compositions comprise a compound of the invention admixed with at least one pharmaceutically acceptable excipient, and preferably with at least one such excipient other than water or a solvent such as DMSO.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

Injection methods are sometimes appropriate routes for administration of the compounds for systemic treatments and sometimes also for localized treatments. These include methods for intravenous, intramuscular, subcutaneous, and other methods for internal delivery that bypass the mucosal and dermal barriers to deliver the composition directly into the subject's living tissues.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677. The present compositions can be utilized in such controlled-release delivery systems where appropriate.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, and the like as in understood in the art. Selection of a particular route for a given subject is well within the ordinary level of skill in the art. For example, rectal delivery as a suppository is often appropriate where the subject experiences nausea and vomiting that precludes effective oral delivery. Transdermal patches are commonly capable of delivering a controlled-release dosage over several days or to a specific locus, and are thus suitable for subjects where these effects are desired.

Transmucosal delivery is also appropriate for some of the compositions and methods of the invention. Thus the compositions of the invention may be administered transmucosally using technology and formulation methods that are known in the art.

For administration to animal or human subjects, the dosage of a compound of the invention is typically 10-2400 mg per administration. However, dosage levels are highly dependent on the nature of the condition, the condition of the patient, the judgment of the practitioner, and the frequency and mode of administration. Selection of a dosage of such compounds is within the skill of an ordinary artisan, and may be accomplished by starting at a relatively low dosage and increasing the dosage until an acceptable effect is achieved.

EXAMPLE 1

The following enumerated embodiments are presented it illustrate certain aspects of the present invention, and are not intended to limit its scope.

1. A compound of formula (1):

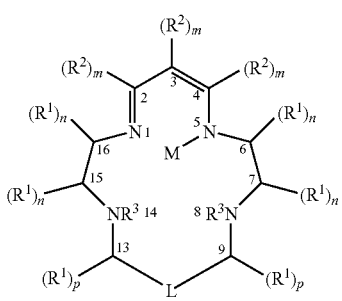

(1)

wherein:

each $R^1$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, =O, OR, $S(O)_tR$, $NR_2$, COOR, $CONR_2$, wherein t can be 0-2 and each R independently represents H, C1-C4 alkyl, and wherein two R groups on one N can cyclize to form a saturated azacyclic group;

each $R^2$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, OR, $S(O)_tR$, $NR_2$, COOR, $CONR_2$, wherein t can be 0-2 and each R independently represents H, C1-C4 alkyl, and wherein two R groups on one N can cyclize to form a saturated azacyclic group;

each $R^3$ is H or a protecting group;

wherein any two $R^1$ on a single carbon can cyclize to form a ring having 3-8 ring atoms, which ring can be substituted, and which can contain a heteroatom selected from N, O and S as a ring member;

and any two $R^1$ on adjacent carbon atoms, and any two $R^2$ groups on adjacent carbon atoms, can cyclize to form a ring having 3-8 ring atoms, which ring can be substituted and can be aromatic or non-aromatic, and can contain a heteroatom selected from N, O and S as a ring member;

and any two of $R^1$ and $R^2$ on carbon atoms separated by a single Nitrogen atom can cyclize to form a ring having 3-8 atoms, which ring can be substituted and can be aromatic or non-aromatic, and can contain, in addition to the N between the carbon atoms to which linked groups are attached, an additional heteroatom selected from N, O and S as a ring member;

each m is independently 0 or 1;

each n and p is independently 0-2;

L represents a three-atom linker that may be $—C(R^1)_p—NR^3—C(R^1)_p—$ or an optionally substituted pyridine-2,6-diyl group; and M represents H or a metal cation;

or a pharmaceutically acceptable salt thereof.

2. The compound of embodiment 1, wherein M is a metal cation.

3. The compound of embodiment 2, wherein the metal cation is Mn (III) or Mn(II).

4. The compound of any of embodiments 1-3, wherein each p is 0.

5. The compound of any of embodiments 1-4, wherein n is 1 for position 6 and position 7, or wherein n is 1 for position 15 and position 16.

6. The compound of embodiment 5, wherein n is 1 for positions 6 and 7, and wherein $R^1$ groups at positions 6 and 7 cyclize to form a 5-8 membered optionally substituted ring.

7. The compound of embodiment 6, wherein n is 1 for positions 15 and 16, and wherein $R^1$ groups at positions 15 and 16 cyclize to form a 5-8 membered optionally substituted ring.

8. The compound of embodiment 7, wherein M represents Mn(III).

9. The compound of any of embodiments 1-8, wherein two $R^1$ groups on adjacent carbon atoms are in a trans orientation relative to each other on the 16-membered ring of formula (1).

10. The compound of embodiment 9, wherein two $R^1$ groups at positions 6 and 7 are in a trans orientation relative to each other on the 16-membered ring of formula (1), and wherein two $R^1$ groups at positions 15 and 16 are also in a trans orientation relative to each other on the 16-membered ring of formula (1).

11. The compound of embodiment 10, wherein two $R^1$ groups at positions 6 and 7 cyclize to form a cyclohexane or cyclopentane ring.

12. The compound of embodiment 11, wherein two $R^1$ groups at positions 15 and 16 cyclize to form a cyclohexane or cyclopentane ring.

13. The compound of embodiment 3, wherein each n is 1, and each p is 0.

14. A compound of formula (2a):

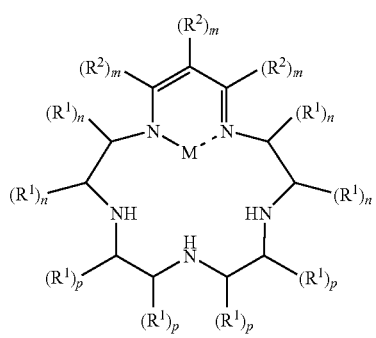

(2a)

wherein $R^1$, $R^2$, m, n, p and M are as defined for formula (1).

15. A compound of formula (2b):

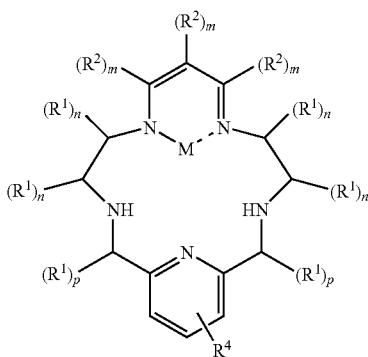

wherein $R^1$, $R^2$, m, n, p and M are as defined for formula (1), and $R^4$ represents one or two optional substituents which may be present at any position(s) on the pyridine ring.

16. The compound of embodiment 14 or embodiment 15, wherein each p is 0.

17. The compound of embodiment 16, wherein two $R^1$ groups are in a trans orientation relative to each other on the 16-membered ring of formula (1), and wherein said two $R^1$ groups cyclize to form a five or six membered ring.

18. The compound of embodiment 17, wherein M is Mn(III).

19. A compound of formula (3):

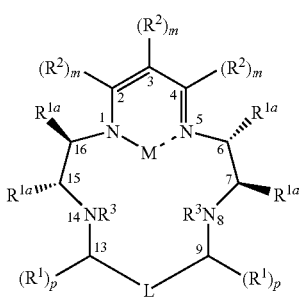

wherein $R^1$, $R^2$, $R^3$, L, m, p and M are as defined above for formula (1), and wherein $R^{1a}$ is an optionally substituted alkyl group, and wherein two $R^{1a}$ groups on adjacent carbons can link to form a ring.

20. The compound of any of embodiments 1-19, wherein M is H.

21. The compound of any of embodiments 1-20, wherein each $R^3$ is H.

22. A method to treat conditions associated with excessive superoxide activity, which method comprises administering to a patient in need of such treatment the compound of any of embodiments 1-21.

23. A pharmaceutical composition comprising a compound according to any of embodiments 1-21, admixed with at least one pharmaceutically acceptable excipient.

24. A method to promote decomposition of superoxide, which comprises adding a compound of any of embodiments 1-21 to a medium containing superoxide or to a medium in which superoxide may be produced.

The foregoing examples are illustrative only, and do not represent any limitation on the scope of the invention. Various modifications and combinations of the features disclosed are apparent to those of skill based on the above disclosure, and those are also within the scope of the invention.

The invention claimed is:

1. A compound of formula (1):

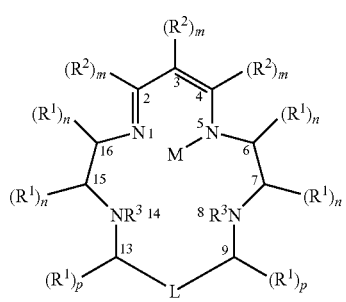

wherein:
each $R^1$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, =O, OR, S(O)$_t$R, NR$_2$, COOR, CONR$_2$, wherein t can be 0-2 and each R independently represents H, C1-4 alkyl, and wherein two R groups on one N can cyclize to form a saturated azacyclic group;

each $R^2$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, OR, S(O)$_t$R, NR$_2$, COOR, CONR$_2$, wherein t can be 0-2 and each R independently represents H, C1-C4 alkyl, and wherein two R groups on one N can cyclize to form a saturated azacyclic group;

each $R^3$ is H or a protecting group;

wherein any two $R^1$ on a single carbon can cyclize to form a ring having 3-8 ring atoms, which ring can be substituted, and which can contain a heteroatom selected from N, O and S as a ring member;

and any two $R^1$ on adjacent carbon atoms, and any two $R^2$ groups on adjacent carbon atoms, can cyclize to form a ring having 3-8 ring atoms, which ring can be substituted and can be aromatic or non-aromatic, and can contain a heteroatom selected from N, O and S as a ring member;

and any two of $R^1$ and $R^2$ on carbon atoms separated by a single Nitrogen atom can cyclize to form a ring having 3-8 atoms, which ring can be substituted and can be aromatic or non-aromatic, and can contain, in addition to the N between the carbon atoms to which linked groups are attached, an additional heteroatom selected from N, O and S as a ring member;

each m is independently 0 or 1;
each n and p is independently 0-2;
L represents a three-atom linker that may be —C(R$^1$)$_p$—NR$^3$—C(R$^1$)$_p$— or an optionally substituted pyridine-2,6-diyl group; and M represents H or a metal cation;
or a pharmaceutically acceptable salt thereof.

2. The compound of claim 1, wherein M is a metal cation.

3. The compound of claim 1, wherein the metal cation is Mn (III) or Mn(II).

4. The compound of claim 1, wherein each p is 0.

5. The compound of claim 1, wherein n is 1 for position 6 and position 7, or wherein n is 1 for position 15 and position 16.

6. The compound of claim 5, wherein n is 1 for positions 6 and 7, and wherein $R^1$ groups at positions 6 and 7 cyclize to form a 5-8 membered optionally substituted ring.

7. The compound of claim 6, wherein n is 1 for positions 15 and 16, and wherein $R^1$ groups at positions 15 and 16 cyclize to form a 5-8 membered optionally substituted ring.

8. The compound of claim 6, wherein M represents Mn(III).

9. The compound of claim 1, wherein two $R^1$ groups on adjacent carbon atoms are in a trans orientation relative to each other on the 16-membered ring of formula (1).

10. The compound of claim 9, wherein two $R^1$ groups at positions 6 and 7 are in a trans orientation relative to each other on the 16-membered ring of formula (1), and wherein two $R^1$ groups at positions 15 and 16 are also in a trans orientation relative to each other on the 16-membered ring of formula (1).

11. The compound of claim 10, wherein two $R^1$ groups at positions 6 and 7 cyclize to form a cyclohexane or cyclopentane ring.

12. The compound of claim 11, wherein two $R^1$ groups at positions 15 and 16 cyclize to form a cyclohexane or cyclopentane ring.

13. The compound of claim 2, wherein each n is 1, and each p is 0.

14. The compound of formula (1) having the structure of formulae (2a) or (2b):

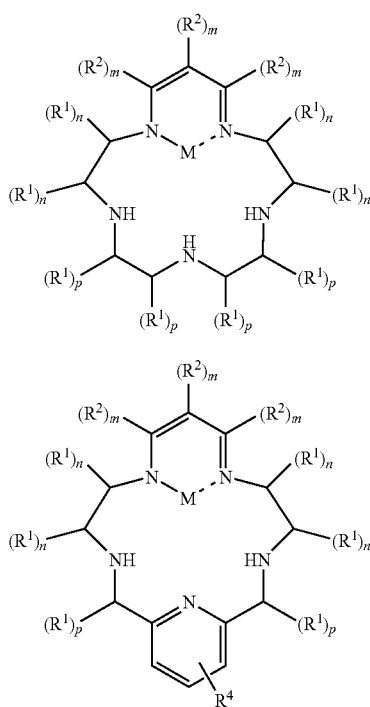

wherein:
each $R^1$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, =O, OR, $S(O)_tR$, $NR_2$, COOR, $CONR_2$, wherein t can be 0-2 and each R independently represents H, C1-C4 alkyl, and wherein two R groups on one N can cyclize to form a saturated azacyclic group;

each $R^2$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, OR, $S(O)_tR$, $NR_2$, COOR, $CONR_2$, wherein t can be 0-2 and each R independently represents H, C1-C4 alkyl, and wherein two R groups on one N can cyclize to form a saturated azacyclic group;

$R^4$ represents one or two optional substituents which may be present at any position(s) on the pyridine ring wherein any two $R^1$ on a single carbon can cyclize to form a ring having 3-8 ring atoms, which ring can be substituted, and which can contain a heteroatom selected from N, O and S as a ring member;

and any two $R^1$ on adjacent carbon atoms, and any two $R^2$ groups on adjacent carbon atoms, can cyclize to form a ring having 3-8 ring atoms, which ring can be substituted and can be aromatic or non-aromatic, and can contain a heteroatom selected from N, O and S as a ring member;

and any two of $R^1$ and $R^2$ on carbon atoms separated by a single Nitrogen atom can cyclize to form a ring having 3-8 atoms, which ring can be substituted and can be aromatic or non-aromatic, and can contain, in addition to the N between the carbon atoms to which linked groups are attached, an additional heteroatom selected from N, O and S as a ring member;

each m is independently 0 or 1;
each n and p is independently 0-2; and
M represents H or a metal cation;
or a pharmaceutically acceptable salt thereof.

15. The compound of claim 14, wherein each p is 0.

16. The compound of claim 15, wherein two $R^1$ groups are in a trans orientation relative to each other on the 16-membered ring of formula (1), and wherein said two $R^1$ groups cyclize to form a five or six membered ring.

17. The compound of claim 16, wherein M is Mn(III).

18. The compound of formula (1) having the structure of formula (3):

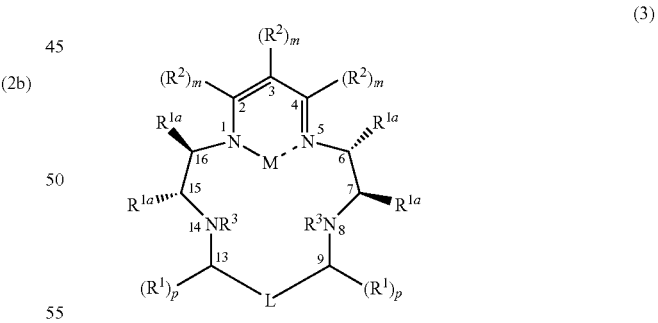

wherein:
each $R^1$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, =O, OR, $S(O)_tR$, $NR_2$, COOR, $CONR_2$, wherein t can be 0-2 and each R independently represents H, C1-C4 alkyl, and wherein two R groups on one N can cyclize to form a saturated azacyclic group;

each $R^2$ is independently C1-C10 alkyl, C6-C10 aryl, C5-C10 heteroaryl, or (C6-C10 aryl)-(C1-C4 alkyl), or (C5-C10 heteroaryl)-(C1-C4 alkyl), each of which can be substituted with one or more groups selected from halo, OR, S(O)$_t$R, NR$_2$, COOR, CONR$_2$, wherein t can be 0-2 and each R independently represents H, C1-C4 alkyl, and wherein two R groups on one N can cyclize to form a saturated azacyclic group;

each R$^3$ is H or a protecting group;

each R$^{1a}$ is an optionally substituted alkyl group and wherein two R$^{1a}$ groups on adjacent carbon atoms can link to form a ring;

wherein any two R$^1$ on a single carbon can cyclize to form a ring having 3-8 ring atoms, which ring can be substituted, and which can contain a heteroatom selected from N, O and S as a ring member;

and any two R$^1$ on adjacent carbon atoms, and any two R$^2$ groups on adjacent carbon atoms, can cyclize to form a ring having 3-8 ring atoms, which ring can be substituted and can be aromatic or non-aromatic, and can contain a heteroatom selected from N, O and S as a ring member;

and any two of R$^1$ and R$^2$ on carbon atoms separated by a single Nitrogen atom can cyclize to form a ring having 3-8 atoms, which ring can be substituted and can be aromatic or non-aromatic, and can contain, in addition to the N between the carbon atoms to which linked groups are attached, an additional heteroatom selected from N, O and S as a ring member;

each m is independently 0 or 1;

each n and p is independently 0-2;

L represents a three-atom linker that may be —C(R$^1$)$_p$—NR$^3$—C(R$^1$)$_p$— or an optionally substituted pyridine-2,6-diyl group; and M represents H or a metal cation;

or a pharmaceutically acceptable salt thereof.

19. The compound of claim 18, wherein M is H.

20. The compound of claim 19, wherein each R$^3$ is H.

21. The compound of claim 1 having a formula selected from the group consisting of:

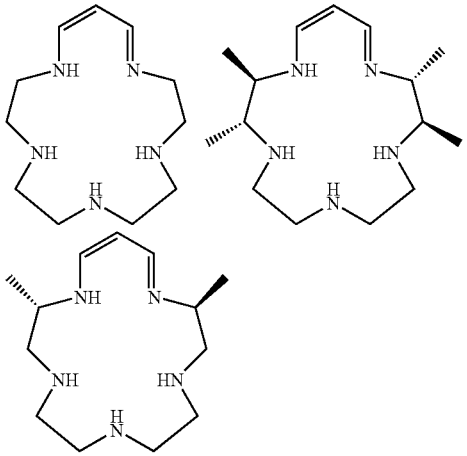

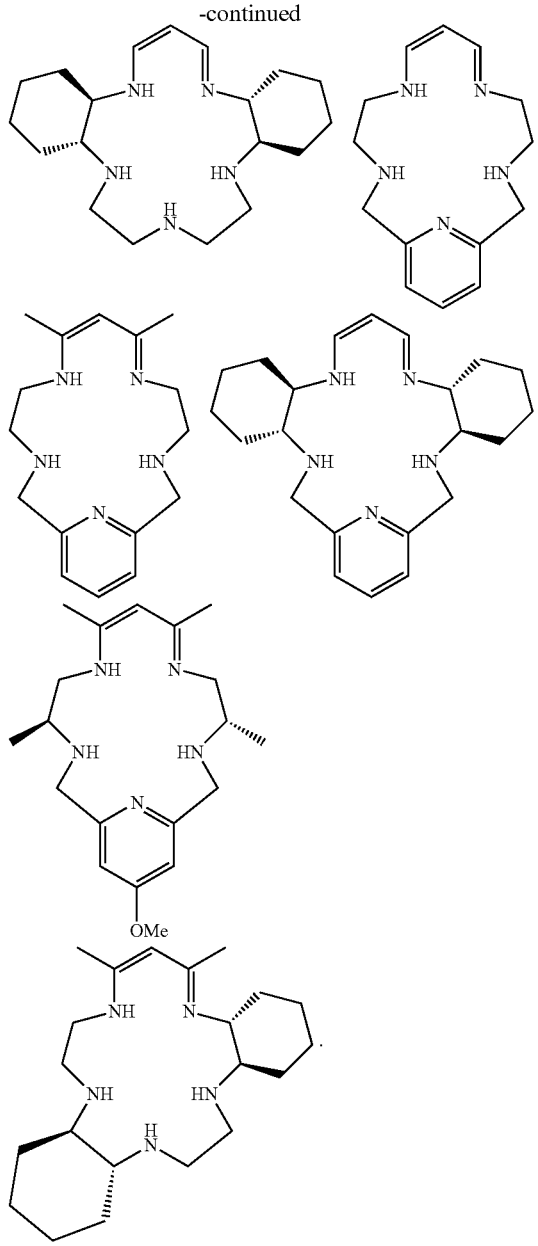

22. A pharmaceutical composition comprising a compound according to claim 1, admixed with at least one pharmaceutically acceptable excipient.

23. A method to promote decomposition of superoxide, which comprises adding a compound of claim 1 to a medium containing superoxide or to a medium in which superoxide may be produced.

* * * * *